United States Patent [19]
Knoll et al.

[11] Patent Number: 4,880,833
[45] Date of Patent: Nov. 14, 1989

[54] SYNERGISTIC PHARMACEUTICAL COMPOSITIONS, THEIR PRODUCTION AND USE

[75] Inventors: József Knoll, Budapest, Hungary; Walter Birkmayer, Vienna, Austria; Katalin Kállóy, Budapest, Hungary; Jenő Marton, Budapest, Hungary; Zoltán Ecsery, Budapest, Hungary

[73] Assignee: Chinoin Gyogyszer Es Vegyeszeti Termekek Gyara RT, Budapest, Hungary

[21] Appl. No.: 908,865

[22] Filed: Sep. 12, 1986

Related U.S. Application Data

[63] Continuation of Ser. No. 684,001, Dec. 20, 1984, abandoned.

[30] Foreign Application Priority Data

Dec. 20, 1983 [HU] Hungary ................ 4343/83

[51] Int. Cl.$^4$ ................ A61K 31/195; A61K 31/16; A61K 31/135
[52] U.S. Cl. ................ 514/565; 514/567; 514/614; 514/654
[58] Field of Search ........... 514/567, 654, 565, 614

[56] References Cited

U.S. PATENT DOCUMENTS

| | | | |
|---|---|---|---|
| 3,362,879 | 1/1968 | Udenfriend et al. | 514/654 |
| 3,485,926 | 12/1969 | Schuler et al. | 514/654 |
| 4,156,017 | 5/1979 | Kruger et al. | 514/654 |
| 4,355,044 | 10/1982 | Heller | 514/567 |
| 4,377,595 | 3/1983 | Wurtman | 514/567 |
| 4,431,670 | 2/1984 | Heller | 514/567 |

OTHER PUBLICATIONS

The Merck Index, 9th ed., abstract No. 7071, (1976).
Chem. Abst., #98:214619f, (1983).
Lysine, Tryptophan and Other Amino Acids, Garrison, Robert Jr. ©1982, pp. 1–9.
L-Deprenyl plus L-Phenylalanine in the Treatment of Depression, Birkmayer et al., J. Neural, Transmission, 59, pp. 81–87, (Springer-Verlag 1984);
Biochemical Effects of Deprenyl, Liebowitz et al, Physchopharmacology Bulletin, vol. 19, No. 3, pp. 337–339, (1983).
Symptoms of Atypical Depression as a Predictor of Response to L-Deprenyl, Mann et al, Psychopharmacology Bulletin, vol. 19, No. 3, pp. 333–335, (1983).
Clinical Efficacy of Deprenyl, a Specific Inhibitor of MAO$_B$; A Double-Blind Placebo Study of L-Deprenyl in Affective Disorders; Mendlewicz et al., Physicopharmacology Bulletin, vol. 19, No. 3, pp. 329–332, (1983).
Chemical Abstracts 100:168070e;
Chemical Abstracts 97:49652f.

Primary Examiner—Douglas W. Robinson
Assistant Examiner—Raymond J. Henley, III
Attorney, Agent, or Firm—Herbert Dubno; Jonathan Myers

[57] ABSTRACT

The invention relates to a synergistic pharmaceutical composition, which comprises as an active ingredient a combination of 1-phenylalanine and (−)-deprenyl [(−)-N-(1-phenylisopropyl)-N-methyl-N-propinylamine hydrochloride] and optionally carbidopa [3-(3,4-dihydroxyphenyl)-2-hydrazino-2-methyl-propionic acid monohydrate] or benzerazide [N-(DL-seryl)-N'-( 2,3,4-trihydroxybenzyl)-hydrazine] in association with conventional inert, non-toxic solid or liquid pharmaceutical carriers. The invention further relates to the preparation of these compositions and to the use thereof for the treatment of depressive symptoms.

8 Claims, No Drawings

SYNERGISTIC PHARMACEUTICAL COMPOSITIONS, THEIR PRODUCTION AND USE

This is a continuation of co-pending application Ser. No. 684,001 filed on Dec. 20, 1984 now abandoned.

It is known that the symptoms of depression can be eliminated by a d-phenylalanine treatment in 60 to 70% of the cases [Fischer et al.: Arzneim. Forsch. 25, 132 (1975); Spatz et al.: Biol. Psychiat. 10, 235–238 (1975)], while d,1-phenylalanine when administered in a daily dose of at most 200 mg, is effective in 60% of the cases [Beckmann et al.: J. neural Transm. 41, 123–134 (1977)]. During the treatment of parkinsonian patients with 1-phenylalanine infusion it has been observed that dysphoria, which is a concomitant phenomenon of Parkinson's disease, is decreased [Birkmayer: Wiener Zeitsch. für Nervenheilkunde 13, 128–139 (1966)].

In earlier open clincal tests [Varga and Tringer: Acta med. Acad. Sci. Hung. 23, 289–295 (1967)] a substantial improvement was achieved in depression clincal pictures by the administration of (±)-deprenyl [i.e. N-(1-phenylisopropyl)-N-methyl-N-propinylamine.HCl] in daily doses of 50 to 100 mg.

(−)-Deprenyl is a potent specific monoaminoxidase B enzyme inhibiting compound, while the (+)-isomer primarily has an amphetamine activity and is essentially responsible for the antidepressive effect of the racemate reported in early publications.

The antidepressive activity of (−)-deprenyl has been examined by many authors. Mann et al. [Life Sci. 26, 877–882 (1980); J. Clin. Psychopharm. 2, 54–57 (1982)] found an antidepressive activity at daily doses of 15 mg and 20 mg, respectively. Mendlewicz et al. [J. neural. Transm. 43, 279–286 (1978); J. Affective Disorders 2, 137–146 (1980)] administered the same compound in a daily dose of 15 mg, in combination with 3×300 mg of 5-OH-tryptophan and 3×75 mg of benzerazide and observed antidepressive activity, just like Liebowitz et al. (International Jumex Conference, May 5–8, 1982 Szombathely) who administered (−)-deprenyl in a daily dose of 30 mg. Others, such as Mendis et al. [Psychopharmacology 73, 87–90 (1981)] did not find a better antidepressive activity than in case of a placebo, when the compound was administered in a daily dose of 20 mg.

We have found that at a simultaneous administration of 1-phenylalanine (200–300 mg, preferably 250 mg, daily) and (−)-deprenyl employed in the selective monoaminoxidase B enzyme inhibiting range (3–10 mg, preferably 5–10 mg, daily) and optionally carbidopa [i.e. 3-(3,4-dihydroxyphenyl)-2-hydrazino-2-methyl-propionic acid monohydrate] in a daily dose of 20–30 mg or benzerazide [i.e. N-(DL-seryl)-N'-(2,3,4-trihydroxybenzyl)-hydrazine] in a daily dose of 50–70 mg there can be observed a substantial increase of therapeutic antidepressive activity.

TEST METHODS

Ambulant treatment: In this group 102 (44 male and 58 female) patients suffering from unipolar, chronic depression for 3 to 15 years were treated. The patients have suffered at least five depressive phases and the antidepressant treatments employed earlier proved ineffective for the treatment of their disease. A combination of 250 mg of 1-phenylalanine and 5–10 mg of (−)-deprenyl was administered orally, in a single dose each morning, for 28 to 96 subsequent days.

Treatment of inpatients: In this group 53 (23 male and 30 female) patients suffering from grave, unipolar, chronic depression for 3 to 15 years were treated. The patients had suffered at least five depressive phases and the conventional antidepressant treatments they had received earlier were ineffective also in their case. A combination of 250 mg of 1-phenylalanine and 10 mg of (−)-deprenyl was administered intravenously, in a single dose each morning, for 14 to 28 subsequent days.

The symptoms of depression were evaluated quantitatively on the basis of a scale widely used in the international literature [Hamilton: J. Neurol. Neurosurg. Psychiat. 23, 56–61 (1960)], by our own method [Birkmayer et al.: In: Masked Depression, Kielholz, P., ed., H. Huber Verlag, Bern-Stuttgart-Wien (1973)] and by the method of clinical, global estimation.

The explanation of the potent synergistic activity of the combined treatment is that 1-phenylalanine as a precursor and (−)-deprenyl by its selective monoaminoxidase B enzyme inhibiting and uptake inhibiting activity regulate the level of cerebral amines in that way that the two effects of similar directions mutually potentiate each other.

The results are set forth in Table 1 below:

TABLE 1

| Oral and intravenous treatment of unipolar depression with 1-phenylalanine and (−)-deprenyl | | |
|---|---|---|
| Parameters of treatment | oral treatment | intravenous |
| duration of depression (years) | 3–15 | 3–15 |
| duration of combined treatment (days) | 28–96 | 14–28 |
|  |  | 14–28 |
| 1-phenylalanine dose (mg/day) | 250 | 250 |
| (−)-deprenyl dose (mg/day) | 5–10 | 10 |
| Result of treatment |  |  |
| first signs of improvement (after ... weeks) | 1 to 3 | 1 to 3 |
| Improvement/recovery in % of total number of patients |  |  |
| cured | 68.5 | 69.5 |
| improved | 21.5 | 11.0 |
| no improvement | 6.0 | 12.0 |
| not evaluated | 4.0 | 7.5 |

The evaluation has been carried out by the method of Birkmayer et al. (see the description of the test method). The average age of patients was 45 years (18–80), in both groups 60% of patients were women. The conventional antidepressive treatments were unsuccessful for these patients.

In the synergistic pharmaceutical compositions according to the invention the weight ratio of the components can be varied within a wide range. Generally 10–70 parts by weight, preferably 25 to 50 parts by weight of 1-phenyl-alanine are employed per 1 part by weight of (−)-deprenyl. The benzerazide component is used in an amount of 5 to 12 parts by weight, the carbidopa in an amount of 2 to 6 parts by weight related to (−)-deprenyl.

According to the invention the new synergistic compositions may be transformed into conventional pharmaceutical compositions suitable for oral, parenteral, intravenous, etc. administration. The formulations are preferably prepared in the form of tablets, coated tablets, dragées, capsules or injections by conventional techniques used for the preparation of pharmaceutical compositions.

The tablets or injection preparations according to the invention preferably contain 250 mg of l-phenylalanine and 5 to 10 mg of (−)-deprenyl.

Further details of the invention are illustrated by the following non-limiting Examples.

Example 1

| Dragee Core | |
|---|---|
| (−)-deprenyl hydrochloride | 5.0 mg |
| l-phenylalanine | 187.5 mg |
| lactose | 115.0 mg |
| starch | 15.5 mg |
| polyvidone | 20.0 mg |
| magnesium stearate | 7.0 mg |
| | 350.0 mg |
| Coating | |
| luviscol VA 64 | 13.0 mg |
| talc | 10.0 mg |
| titanium dioxide | 20.0 mg |
| Carbowax 6000 | 7.0 mg |
| | 50.0 mg |

Example 2

| Dragee core | |
|---|---|
| (−)-deprenyl hydrochloride | 5.0 mg |
| l-phenylalanine | 50.0 mg |
| lactose | 70.0 mg |
| starch | 9.5 mg |
| polyvidone | 12.5 mg |
| magnesium stearate | 3.0 mg |
| | 150.0 mg |
| Coating | |
| methocel 60 Hg 15 cP | 8.0 mg |
| talc | 6.0 mg |
| titanium dioxide | 12.0 mg |
| Carbowax 6000 | 4.0 mg |
| | 30.0 mg |

Example 3

| Dragee core | |
|---|---|
| (−)-deprenyl | 5.0 mg |
| l-phenylalanine | 250.0 mg |
| lactose | 92.5 mg |
| starch | 19.0 mg |
| polyvidone | 25.5 mg |
| magnesium stearate | 8.0 mg |
| | 400.0 mg |
| Coating | |
| luviscol VA 64 | 6.5 mg |
| methocel 60 Hg 16 cP | 6.5 mg |
| talc | 10.0 mg |
| titanium dioxide | 22.0 mg |
| Carbowax 6000 | 5.0 mg |
| | 50.0 mg |

PREPARATION

The components according to the above Examples are weighed separately in amounts required for the preparation of 10,000 dragée cores. The two active ingredients are homogenized with the total amount of lactose. Polyvidone is dissolved in 96% ethanol with slight heating. The homogenizate of the active ingredients and lactose is knead thoroughly and homogenized with the above granulating solution, in a suitable apparatus. The granulate is dried at a temperature up to 35° C. until the required degree of humidity is achieved, and is then regranulated. To the granulate obtained starch is added, and biconvex dragée cores are pressed weighing 150, 350 and 400 mg, respectively. The coating suspension is prepared by homogenizing the components of the coating, and subsequently dissolving the mixture obtained in isopropanol. The coating is applied to the spinned dragée cores by pneumatic sprayer. The coating is dried by an air stream of 35° C. The dragées are polished with a 1:1 mixture of isopropanol and water, containing 10% of Carbowax, and packed in a conventional manner.

Example 4

| (−)-deprenyl hydrochloride | 5.0 mg |
|---|---|
| l-phenylalanine | 250.0 mg |
| carbidopa (equivalent to 25.0 mg of carbidopa anhydrate) | 27.0 mg |
| lactose | 25.5 mg |
| starch | 14.5 mg |
| polyvidone | 20.0 mg |
| magnesium stearate | 8.0 mg |
| | 350.0 mg |

Example 5

| (−)-deprenyl hydrochloride | 5.0 mg |
|---|---|
| l-phenylalanine | 250.0 mg |
| benzerazide hydrochloride (corresponding to 62.5 mg of benzerazide) | 71.25 mg |
| lactose | 23.75 mg |
| starch | 22.0 mg |
| polyvidone | 20.0 mg |
| magnesium stearate | 8.0 mg |
| | 400.0 mg |

PREPARATION OF THE ABOVE COMBINATIONS

From the components granulate is prepared as described in Examples 1 to 3, which is then filled into capsules of appropriate size in a suitable equipment, and packed in a known manner.

We claim:

1. A synergistic pharmaceutical composition for the treatment of depression which comprises a therapeutically effective amount of a combination of:
   25 to 50 parts by weight of l-phenylalanine; and
   1 part by weight of (−)-deprenyl, or the hydrochloride acid addition salt thereof; and a pharmaceutically acceptable inert, nontoxic carrier.

2. The synergistic pharmaceutical composition defined in claim 1 which further comprises 5 to 12 parts by weight of benserazide.

3. The synergistic pharmaceutical composition defined in claim 1 which further comprises 2 to 6 parts by weight of carbidopa.

4. The synergistic pharmaceutical composition defined in claim 1 in a form suitable for oral or parenteral administration.

5. The synergistic pharmaceutical composition defined in claim 1 in tablet form containing 250 mg of l-phenylalanine and 5 to 10 mg of (−)-deprenyl or the hydrochloride acid addition salt thereof.

6. The synergistic pharmaceutical composition defined in claim 1 in injectable form containing 250 mg of l-phenylalanine and 10 mg of (−)-deprenyl or the hydrochloride acid addition salt thereof.

7. A method of treating depression in a human patient which comprises the step of orally administering to the human patient a daily dosage of 250 mg of l-phenylalanine and 5 to 10 mg of (−)-deprenyl or the hydrochloride acid addition salt thereof.

8. A method of treating depression in a human patient which comprises the step of intravenously administering to the human patient a daily dosage of 250 mg of l-phenylalanine and 10 mg of (−)-deprenyl or the hydrochloride acid addition salt thereof.

* * * * *